(12) United States Patent
Fuchs et al.

(10) Patent No.: US 9,381,324 B2
(45) Date of Patent: Jul. 5, 2016

(54) IV-CATHETER INSERTION DEVICE

(71) Applicant: B. BRAUN MELSUNGEN AG, Melsungen (DE)

(72) Inventors: Juergen Fuchs, Bad Emstal (DE); Hermann Riesenberger, Bebra (DE)

(73) Assignee: B. Braun Melsungen AG, Melsungen (DE)

( * ) Notice: Subject to any disclaimer, the term of this patent is extended or adjusted under 35 U.S.C. 154(b) by 468 days.

(21) Appl. No.: 13/962,503

(22) Filed: Aug. 8, 2013

(65) Prior Publication Data

US 2013/0324930 A1 Dec. 5, 2013

Related U.S. Application Data

(63) Continuation of application No. 13/508,963, filed as application No. PCT/EP2010/006909 on Nov. 12, 2010, now Pat. No. 8,535,271.

(30) Foreign Application Priority Data

Nov. 12, 2009 (DE) .......................... 10 2009 052 962

(51) Int. Cl.
*A61M 5/178* (2006.01)
*A61M 25/06* (2006.01)
*A61M 5/32* (2006.01)

(52) U.S. Cl.
CPC ......... *A61M 25/0631* (2013.01); *A61M 5/3257* (2013.01); *A61M 2005/325* (2013.01)

(58) Field of Classification Search
CPC ............ A61M 5/3273; A61M 5/3275; A61M 2005/325; A61M 25/0631; A61M 5/3257
See application file for complete search history.

(56) References Cited

U.S. PATENT DOCUMENTS 4,944,725 A 7/1990 McDonald
5,215,525 A 6/1993 Sturman
(Continued)

FOREIGN PATENT DOCUMENTS

EP 0 799 626 A1 10/1997
EP 1 486 225 A1 12/2004

OTHER PUBLICATIONS

International Search Report completed Feb. 8, 2011 and mailed Feb. 16, 2011 from related International Application No. PCT/EP2010/006909 filed Nov. 12, 2010 (3 pages).
(Continued)

*Primary Examiner* — Aarti B Berdichevsky
(74) *Attorney, Agent, or Firm* — Klein, O'Neill & Singh, LLP

(57) ABSTRACT

The present disclosure is directed to a catheter insertion device, which has a catheter hub at the proximal end of a catheter, a tubular needle hub, at which a hollow needle is fixed and extends through the catheter hub and the catheter in a ready position such that the needle tip projects over the distal end of the catheter, a protective barrel which is received in the tubular needle hub in the ready position and is releasably connected to the catheter hub, and a pressure spring arranged between the needle hub and the protective barrel and which displaces the needle hub and the protective barrel apart from each other in an axial direction, wherein a manually operable holding member is provided between the needle hub and the protective barrel, and holds the needle hub in the ready position at the protective barrel against the bias of the pressure spring, so that after the holding member is released, the pressure spring moves the needle hub into a protective position in relation to the protective barrel, in which position the needle is positioned in the protective barrel.

21 Claims, 5 Drawing Sheets

(56) References Cited

U.S. PATENT DOCUMENTS

| | | | |
|---|---|---|---|
| 5,312,361 A | 5/1994 | Zadini et al. | |
| 5,411,486 A | 5/1995 | Zadini et al. | |
| 5,853,393 A | 12/1998 | Bogert | |
| 6,117,108 A | 9/2000 | Woehr et al. | |
| 6,749,588 B1 | 6/2004 | Howell et al. | |
| 7,044,935 B2 * | 5/2006 | Shue | A61B 5/1438 604/164.01 |
| 7,736,339 B2 | 6/2010 | Woehr et al. | |
| 8,328,762 B2 | 12/2012 | Woehr et al. | |
| 8,535,271 B2 * | 9/2013 | Fuchs | A61M 25/0631 604/164.08 |
| 2002/0169418 A1 * | 11/2002 | Menzi | A61M 25/0637 604/164.07 |
| 2003/0199827 A1 * | 10/2003 | Thorne | A61M 25/0631 604/164.08 |
| 2004/0127854 A1 | 7/2004 | Leinsing et al. | |
| 2005/0101914 A1 | 5/2005 | Shue et al. | |
| 2006/0116638 A1 | 6/2006 | Woehr et al. | |
| 2006/0155245 A1 | 7/2006 | Woehr | |
| 2008/0132846 A1 | 6/2008 | Shue et al. | |
| 2008/0167623 A1 | 7/2008 | Iwase et al. | |
| 2010/0249707 A1 * | 9/2010 | Woehr | A61M 25/0618 604/164.08 |
| 2012/0277680 A1 | 11/2012 | Woehr et al. | |

OTHER PUBLICATIONS

Office Action dated mailed Jan. 22, 2013 from related U.S. Appl. No. 13/508,963, filed May 9, 2012.

Notice of Allowance mailed Jul. 2, 2013 from related U.S. Appl. No. 13/508,963, filed May 9, 2012.

* cited by examiner

IV-CATHETER INSERTION DEVICE

CROSS-REFERENCE TO RELATED APPLICATIONS

This is a continuation application of application Ser. No. 13/508,963, filed May 9, 2012, §371 date of Jun. 26, 2012, which is a national phase application under 35 U.S.C. §371 of PCT Application No. PCT/EP2010/006909 filed Nov. 12, 2010, which claims the benefit of German application No. 10 2009 052 962.4 filed Nov. 12, 2009, the contents of each of which are expressly incorporated herein by reference.

FIELD OF ART

The present disclosure relates to a IV-catheter insertion device, comprising a protective barrel attached releasably to the catheter hub of an IV-catheter including a catheter hub, a catheter tube and a hollow needle extending through the lumen of the catheter tube in a ready position, whereby the hollow needle is received into the protective barrel in a protective position after the protective barrel is released from the catheter hub.

SUMMARY

In accordance with the first preferred embodiment of the IV-catheter insertion device of the present disclosure a tubular needle holder surrounds the protective barrel and a spring is provided between the protective barrel and needle holder. The tension of the spring is released by triggering a holding member, so that the hollow needle is automatically retracted into the protective barrel. This leads to simple handling combined with a reliable protection against needle-stick injuries In a further preferred embodiment of the IV-catheter insertion device according to the present method, system and device, a spring clip is held at the distal end of the protective barrel. In the protective position, the hollow needle is retracted into the protective barrel and the needle tip is additionally covered by the spring clip.

Furthermore, a preferred embodiment of the IV-catheter insertion device according to the method, system and device has a self-closing valve, by means of which leakage of blood from the catheter hub after the removal of the hollow needle can be prevented.

Further aims, advantages, features and possible applications of the present method, system and device become apparent from the following description of the embodiments with reference to the drawings. Hereby, all the features described and/or shown diagrammatically form the subject matter of the present method, system and device, whether in themselves or in any meaningful combination, and independently of their summary in the claims and of the back-referencing of the claims.

BRIEF DESCRIPTION OF THE FIGURES

Examples of the present method, system and device are explained in more detail below with reference to the drawing, in which.

DETAILED DESCRIPTION

Figure 1:
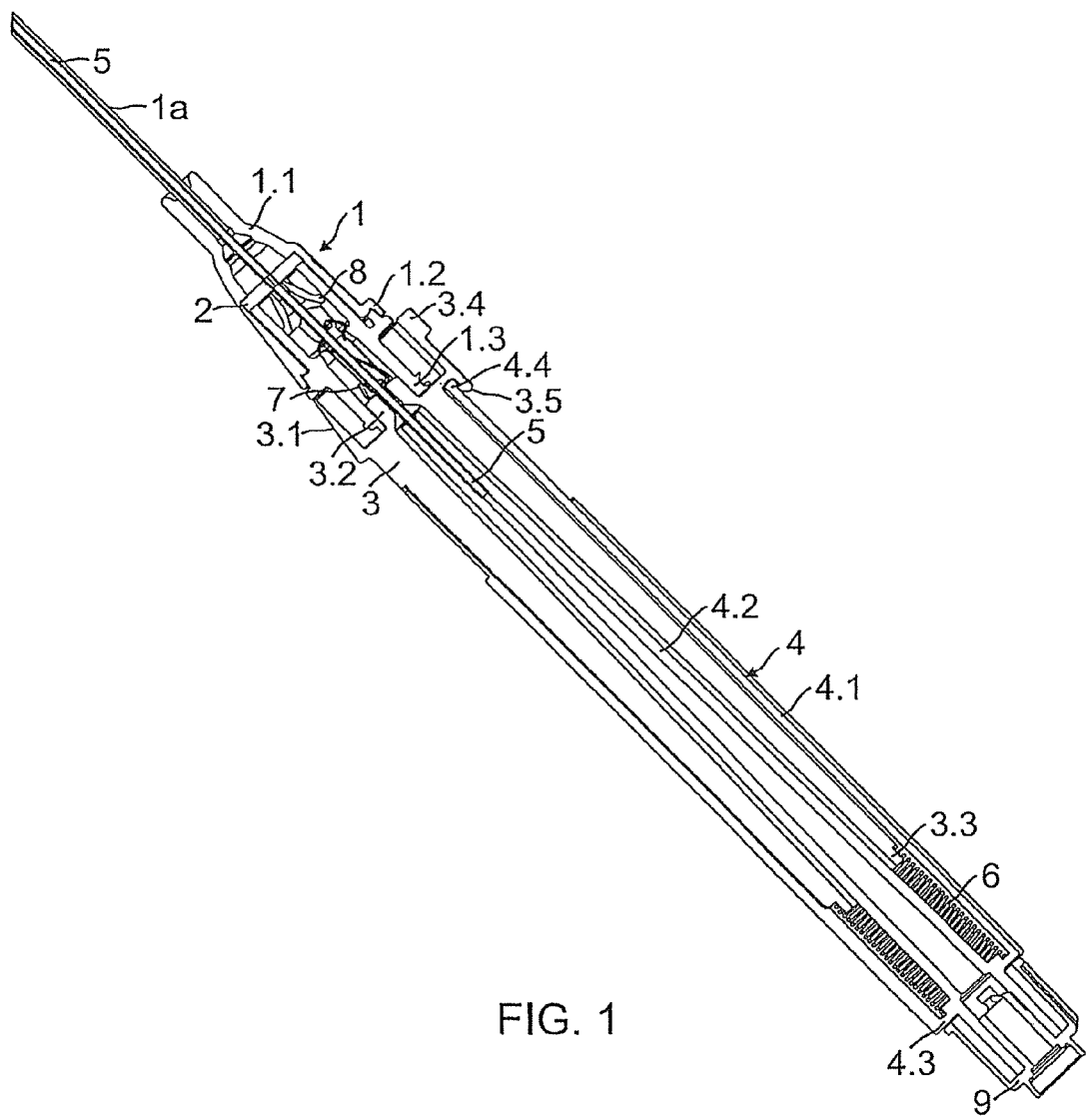
FIG. 1 shows a longitudinal section through the IV-catheter insertion device in a ready position.

In the Figures, reference numeral 1 refers to a catheter hub which, in the embodiment shown, comprises a distal part 1.1 and a proximal part 1.2, between which an automatically self-closing valve 2 in the form of a valve disc is held, the valve 2 being provided with a central slit or slits which extend preferably radially out from the centre of the valve 2 and which is or which are closed in the closed position of the valve. At the distal end of the catheter hub 1, a catheter tube la is held in the hub part 1.1, preferably by a metal bushing. At the proximal end of the catheter hub 1, a Luer thread 1.3 is formed at the catheter hub part 1.2. The two parts 1.1 and 1.2 of the catheter hub 1 are joined to each other by bonding or welding. However, it is also possible to provide a one-piece catheter hub 1.

Figure 5:
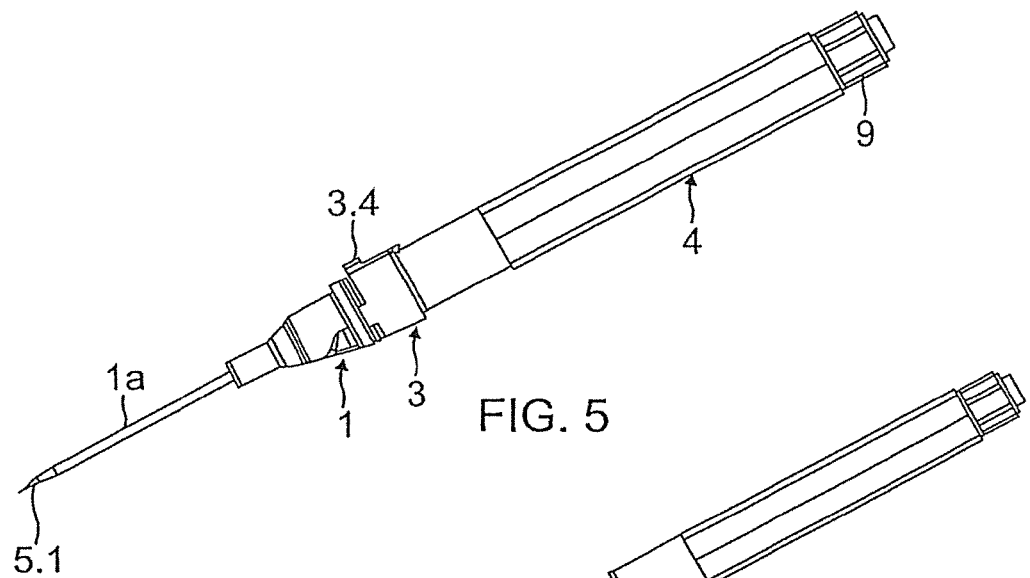
FIG. 5 shows a side view of the IV-catheter insertion device in the ready position.

In the ready position of FIGS. 1 and 5, a protective barrel 3 is joined to the catheter hub 1, and the collar-shaped distal end 3.1 of this protective barrel overlaps the Luer thread 1.3 of the catheter hub 1 and engages with the proximal end of the catheter hub 1 by means of a central hub 3.2.

The protective barrel 3 is received in a needle holder 4 in the ready position of FIGS. 1 and 5, and the outer housing 4.1 of this needle holder surrounds the outer circumference of the protective barrel 3 and is joined to a hollow central hub 4.2 at the proximal end via a radial transverse wall 4.3, wherein a hollow needle 5 is fixed in the distal end of this hub, for example by bonding, and in the ready position of FIGS. 1 and 5, this hollow needle extends through the valve 2 and the catheter 1a, so that the needle tip 5.1 (FIG. 5) protrudes at the distal end of the catheter tube 1a. In the embodiment shown, the hollow central hub 4.2 extends from the proximal transverse wall 4.3 essentially up to the front end of the outer housing 4.1 of the needle holder 4.

The proximal end 3.3 of the protective barrel 3 lies at a distance from the transverse wall 4.3 of the needle holder 4. A pressure spring 6 is arranged between the transverse wall 4.3 and the proximal end 3.3 of the protective barrel 3, whereby the proximal end acts as a support for the pressure spring 6.

Figure 3:
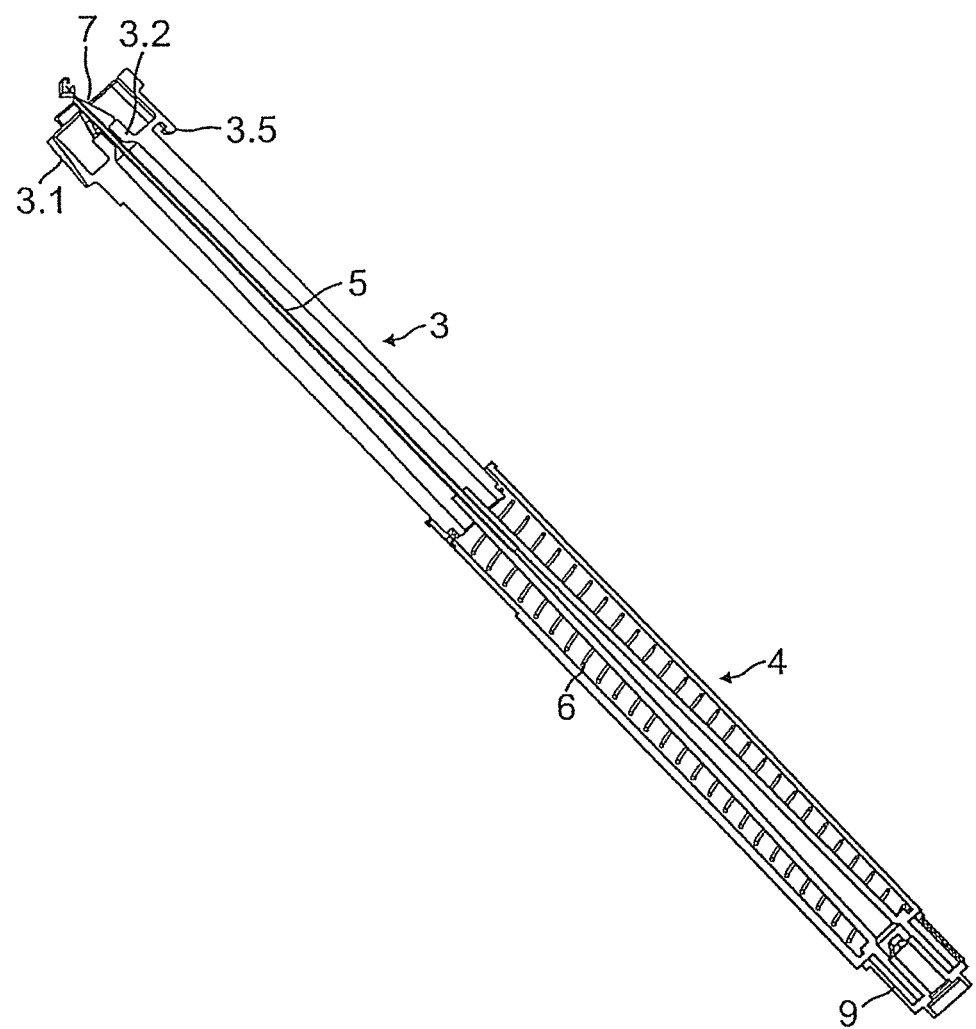
FIG. 3 shows a longitudinal section through the protective position of the protective barrel.
Figure 6:
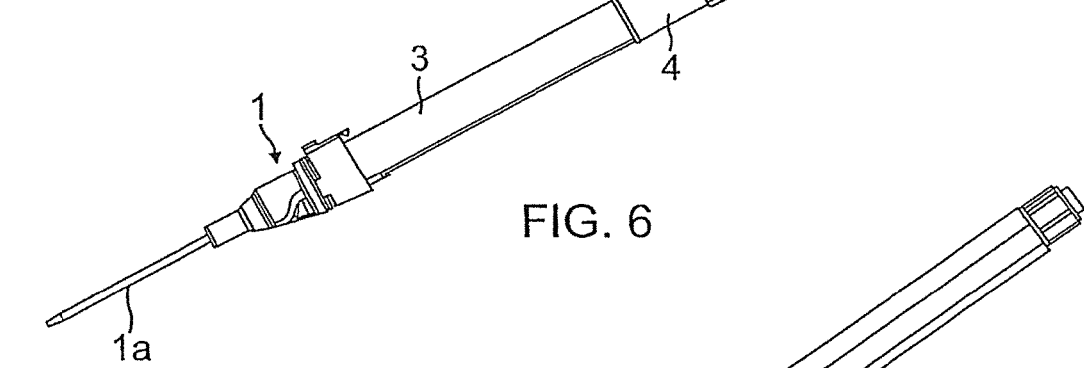
FIG. 6 shows a view of the IV-catheter insertion device in the protective position.

At the distal end of the protective barrel 3, preferably in the area of the collar portion 3.1, a radially movable lever portion 3.4 is formed, which is joined to a retaining hook 3.5 which, in the ready position of FIG. 1, overlaps a radial projection or flange 4.4 at the distal end of the housing 4.1 of the needle holder 4. By depressing the lever portion 3.4 in FIG. 1, the hook 3.5 is pivoted radially outwards, so that the needle holder 4 is released and the pressure spring 6 moves the needle holder 4 proximally relative to the protective barrel 3, as FIGS. 3 and 6 show, the distal end of the needle holder 4 still being held at the proximal end of the protective barrel 3. In this protective position of FIGS. 3 and 7, the hollow needle 5 is retracted into the protective barrel 3 and covered by a needle guard element in the form of a spring clip 7 such that the needle tip is no longer exposed and cannot lead to an injury.

In this shown embodiment, the spring clip 7 is held by its proximal rear wall 7.1 at the distal end of the protective barrel 3, preferably by means of moulded-on hooks 3.7 (FIGS. 2 and 4), wherein the spring clip in the embodiment shown is formed as a two-armed spring clip with crossing arms. In the protective position of FIGS. 3 and 6, the needle tip 5.1 is covered by at least one of the distal wall portions 7.2 and 7.3 of the arms of the spring clip 7, so that the hollow needle 5 need not be fully retracted into the protective barrel 3. Alternatively, however, the distal end of the protective barrel 3 can also be formed somewhat longer, so that both the hollow needle and the needle tip are then positioned completely inside the protective barrel in the protective position.

Figure 2:
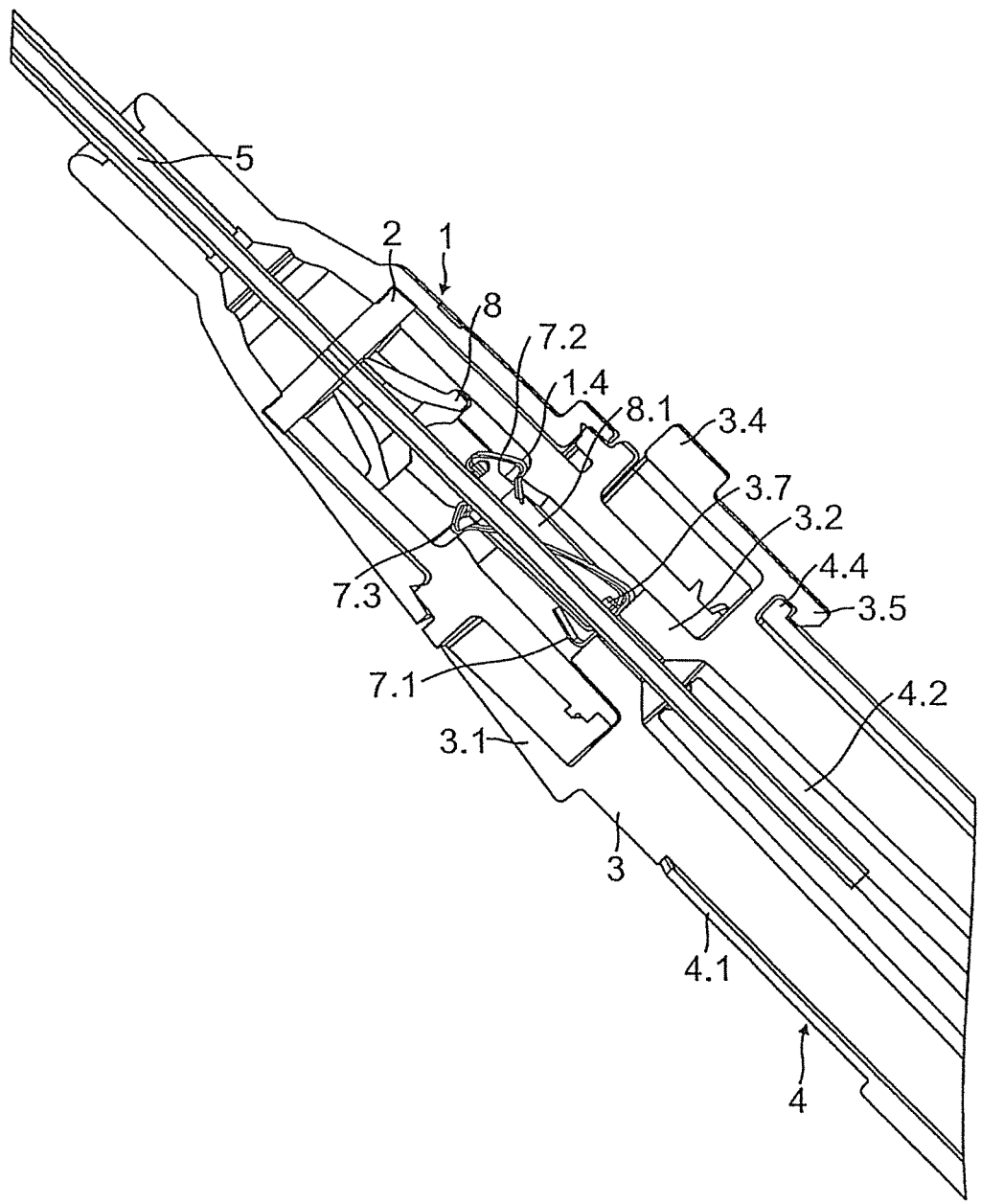
FIG. 2 shows a detailed view of the catheter hub.

The hooks 3.7 holding the spring clip 7 are formed at the front face of the central hub 3.2 of the protective barrel 3. The central hub 3.2 engages the catheter hub 1 in the ready position, as FIG. 2 shows.

In the ready position, elbow-shaped portions at the distal wall portions 7.2 and 7.3 of the arms of the spring clip 7 abut behind a shoulder 1.4 on the inner circumference of the catheter hub 1, so that the spring clip 7 is held in the catheter hub 1 until the needle tip 5.1 is positioned inside the spring clip 7 in the protective position (FIG. 3) and the needle shaft releases the radial spread of the distal wall portions 7.2 and 7.3 of the spring arms of the spring clip. In the protective position, the distal wall portions of the spring clip 7 spring radially inwards so that they are released from the shoulder 1.4 in the catheter hub 1, and the protective barrel 3 with the spring clip 7 held thereon can be released from the catheter hub 1, as FIG. 7 shows.

Near the needle tip 5.1, a crimp (not shown), formed by crimping the needle shaft proximal of the needle tip, or a radial projection (not shown), is formed, which in the protective position in FIG. 3 abuts at the proximal rear wall 7.1 of the spring clip 7 and thereby also holds the needle holder 4 via the needle 5 on the protective barrel 3 in the position as shown in FIG. 3.

Figure 7:
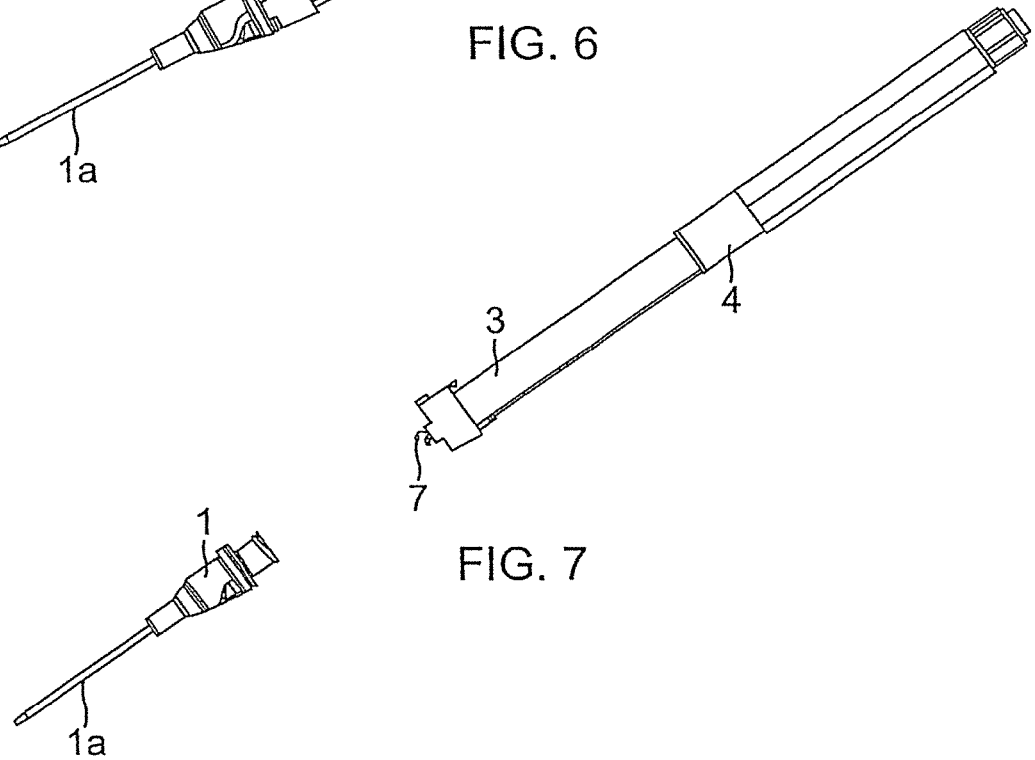
FIG. 7 shows the protective barrel released from the catheter hub.

In alternative embodiments (not shown) without a needle guard element, the distal end of the protective barrel is somewhat longer, or the hollow needle is somewhat shorter than represented in FIGS. 3 and 7, so that both the hollow needle and the needle tip are then positioned completely inside the protective barrel in the protective position. In the embodiments according to the present method, system and device without a needle guard element, the needle can have a needle crimp to hold the needle holder via the hollow needle on the protective barrel. Alternatively, in the case of a hollow needle without a needle crimp, the proximal end of the protective barrel can lock with the distal end of the needle holder.

Thus, in addition to the protective function in relation to the needle tip, the needle guard element in the form of the spring clip 7 fixed to the protective barrel 3 also fulfils two holding functions the first between the catheter hub 1 and the protective barrel 3 and the second between the protective barrel 3 and the needle holder 4 In the ready position of FIG. 1, the spring clip 7 holds the protective barrel 3 abutting the catheter hub 1 as long as the elbows at the distal wall portions 7.2 and 7.3 engage behind the shoulder 1.4 in the catheter hub. This engagement prevents the axial disconnection of the catheter hub 1 from the protective barrel 3 in the ready position, so that the catheter hub 1 and the protective barrel 3, together with the needle holder 4 form a unit in FIGS. 1 and 5. In the protective position of FIG. 3, the spring clip 7 holds the needle holder 4 at the protective barrel 3 against the force of the pressure spring 6 by engagement of the edge of the bore in the proximal rear wall 7.1 of the spring clip with a projection on the needle shaft, so that no further holding means are required between the proximal end of the protective barrel 3 and the distal end of the needle holder 4 in FIGS. 3 and 7 in order for the protective barrel 3 and the needle holder 4 to form a unit on disposal.

In the embodiment of FIGS. 1 and 2, a valve-actuation element 8 is displaceably guided in the catheter hub 1 and has diametrally opposite stays 8.1, between which the spring clip 7 is arranged in the ready position. After the protective barrel 3 is released from the catheter hub 1 (FIG. 7), a syringe or an infusion line can be connected to the catheter hub, wherein a hub formed at the infusion hose or the syringe, corresponding to the central hub 3.2 of the protective barrel 3, displaces the valve actuation element 8 in the distal direction to open the valve 7.

Figure 4:
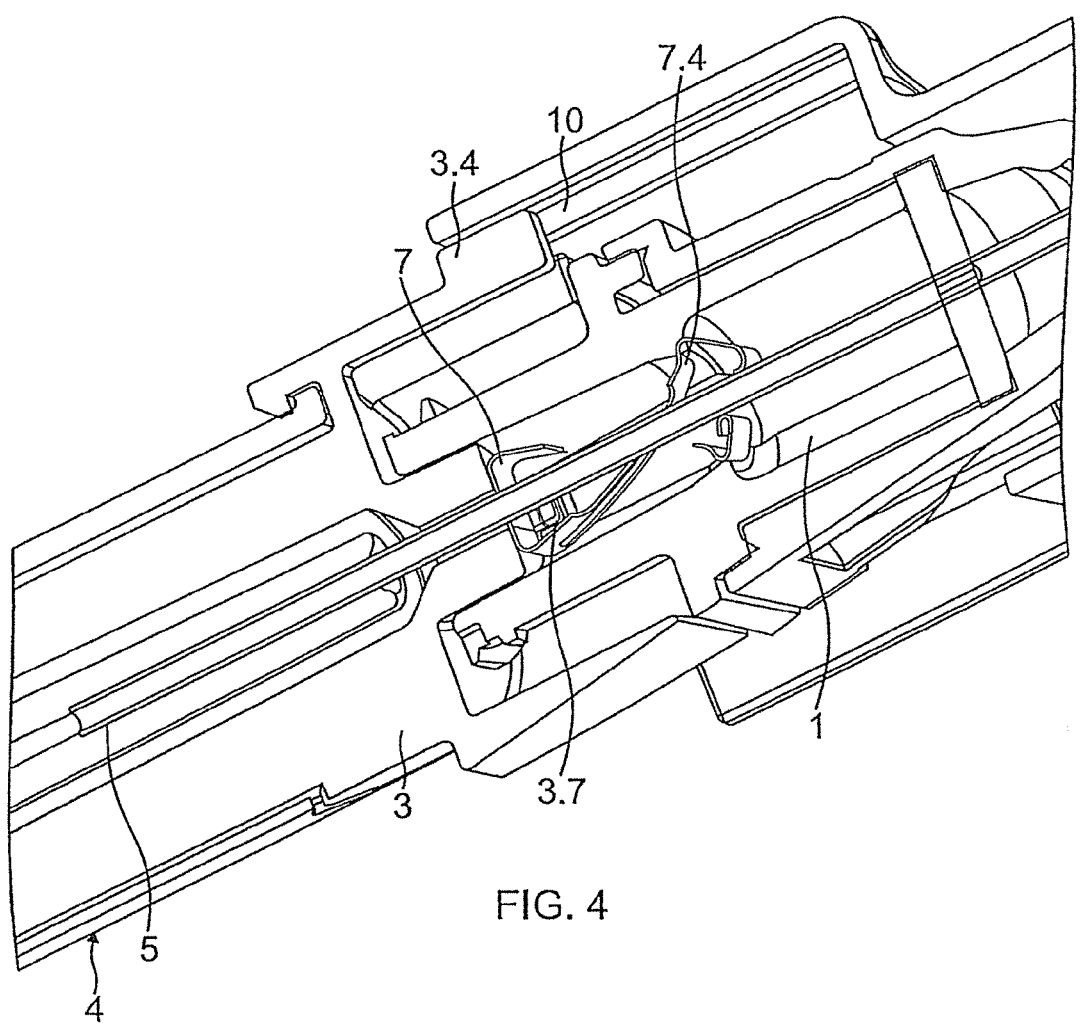
FIG. 4 shows another embodiment of the catheter hub.

In the embodiment of FIG. 4, no valve-actuation element 8 is provided. The valve 2 in the form of a valve disc opens or closes automatically when a liquid is introduced or when blood is collected. Reference numeral 10 of FIG. 4 shows a protective cap attached to the catheter hub 1, preferably covering the lever or press-button 3.4 at the protective barrel so that this lever or press-button can only be actuated after the removal of the protective cap 10.

Further embodiments according to the present method, system and device can also be formed without any valve whatsoever or without any valve with valve actuation element respectively.

The needle holder 4 can be formed with a closed proximal end. In the embodiment according to FIG. 1, the hollow middle hub 4.2 of the needle holder 4 is open at the proximal end and is closed by a blood-stopper 9.

Several modifications of the described embodiments are possible. For example, a holding member can be formed at the distal end of the outer housing 4.1 of the needle holder 4, wherein this holding member releases the connection with the distal end of the protective barrel 3, so that a relative displacement between the needle holder 4 and the protective barrel 3 by the pressure spring 6 is possible.

Instead of a needle guard element in the form of a spring clip with crossing arms, a needle guard element can also be provided, whose two arms extend from the proximal rear wall approximately parallel to each other, whereby the arms of such a spring clip also hold the spring clip in the catheter hub in the ready position as long as the arms of the spring clip are spread apart from each other by the needle shaft.

Further the spring clip 4 can be embodied as another kind of needle guard element. Needle guard elements as shown in WO 99/08742 can be used. Further it is also possible that a sleeve having a rear wall can be used as needle guard element wherein the distal end of the sleeve has radial elasticity by slits which extend parallel to the axis of the sleeve on the distal end which can be provided by an engagement means on the outer circumference for engaging the inner circumference of the catheter hub.

The needle guard element can be made of metal and/or plastic material and can comprise several parts.

The invention claimed is:
1. An IV-catheter insertion device, comprising:
 a catheter hub having a body defining an interior cavity and a catheter tube attached thereto and extending distally thereof;
 a valve positioned in the interior cavity of the catheter hub for restricting flow through the catheter hub, said valve comprising a slit;
 a valve opener slidably positioned in the interior cavity of the catheter hub for opening the slit to permit fluid flow across the valve;
 a needle holder having a hollow needle and a needle tip attached thereto, the hollow needle extending through the catheter hub, the valve, and the catheter tube in a ready position;

a protective barrel comprising a depressible lever or press-button at a distal end of the protective barrel, the depressible lever or press-button engaging a section of the needle holder to retain a pressure spring in a compressed state in the ready position between support surfaces on the protective barrel and the needle holder; and wherein the depressible lever or press-button is releasable from the section of the needle holder when depressed to release the pressure spring to move the hollow needle inside the protective barrel in a protective position.

2. The IV-catheter insertion device according to claim 1, wherein the needle holder comprises an outer needle holder housing and wherein the depressible lever or press-button engages a projection on the outer needle holder housing in the ready position.

3. The IV-catheter insertion device according to claim 1, further comprising a needle guard mounted at a distal end of the needle holder for covering the needle tip in the protective position.

4. The IV-catheter insertion device according to claim 1, wherein the needle holder comprises an outer needle holder housing and wherein the pressure spring is located in an annular space between the outer needle holder housing and a central needle hub.

5. The IV-catheter insertion device according to claim 1, wherein the valve is abutted against a shoulder in the interior cavity of the catheter hub.

6. The IV-catheter insertion device according to claim 1, wherein the valve opener comprises at least two spaced apart stays.

7. The IV-catheter insertion device according to claim 1, wherein the depressible lever or press-button engages a distal section of the needle holder in the ready position.

8. An IV-catheter insertion device, comprising:
a catheter hub having a body defining an interior cavity and a catheter tube attached thereto and extending distally thereof;
a valve positioned in the interior cavity of the catheter hub and against a shoulder for restricting flow through the catheter hub, said valve comprising a slit;
a valve opener positioned in the interior cavity of the catheter hub and in sliding communication with the valve;
a needle holder having a hollow needle with a needle tip attached thereto, the hollow needle extending through the catheter hub, the valve, the valve opener, and the catheter tube in a ready position;
a protective barrel comprising an elongated rigid body having an interior cavity sized and shaped to receive the hollow needle in a protective position;
a pressure spring abutted at a first end by a support surface on the needle holder and at a second end by a support surface on the protective barrel;
a depressible lever or press-button associated with the protective barrel comprising a retainer, which extends radially towards and engages a distal section of the needle holder to compress the pressure spring in the ready position; and
wherein the depressible lever or press-button is releasable from the section of the needle holder when depressed to release the pressure spring to move the hollow needle inside the protective barrel in the protective position.

9. The IV-catheter insertion device according to claim 8, wherein the needle holder comprises an outer needle holder housing and wherein the depressible lever or press-button engages a projection on the outer needle holder housing in the ready position.

10. The IV-catheter insertion device according to claim 8, further comprising a needle guard mounted at a distal end of the needle holder for covering the needle tip in the protective position.

11. The IV-catheter insertion device according to claim 8, wherein the needle holder comprises an outer needle holder housing and wherein the pressure spring is located in an annular space between the outer needle holder housing and a central needle hub.

12. The IV-catheter insertion device according to claim 8, wherein the valve opener comprises at least two spaced apart stays.

13. The IV-catheter insertion device according to claim 8, further comprising a central hub section extending distally of the protective barrel and into the interior cavity of the catheter hub in the ready position.

14. The IV-catheter insertion device according to claim 8, wherein the depressible lever or press-button is pivotably connected to the protective barrel.

15. The IV-catheter insertion device according to claim 8, wherein the retainer is a retaining hook.

16. An IV-catheter insertion device, comprising:
a catheter hub having a body defining an interior cavity and a catheter tube attached thereto and extending distally thereof;
a valve positioned in the interior cavity of the catheter hub for restricting flow through the catheter hub, said valve comprising a slit;
a needle holder having a hollow needle and a needle tip attached thereto, the hollow needle extending through the catheter hub, the valve, and the catheter tube in a ready position;
a protective barrel comprising an elongated rigid body having an interior cavity sized and shaped to receive the hollow needle in a protective position;
a single depressible lever or press-button at a distal end of the protective barrel engaging a distal section of the needle holder to compress a pressure spring abutted at a first end by a support surface on the needle holder and at a second end by a support surface on the protective barrel; the pressure spring being held compressed in the ready position until the single depressible lever or press-button is depressed; and
wherein the pressure spring expands when the single depressible lever or press-button is activated and the needle holder and the hollow needle move in a proximal direction relative to the protective barrel to move the hollow needle inside the protective barrel in the protective position.

17. The IV-catheter insertion device according to claim 16, further comprising a valve opener slidably positioned in the interior cavity of the catheter hub for opening the slit.

18. The IV-catheter insertion device according to claim 16, wherein the needle holder comprises an outer needle holder housing and wherein the depressible lever or press-button engages a projection on the outer needle holder housing in the ready position.

19. The IV-catheter insertion device according to claim 16, further comprising a needle guard mounted at a distal end of the needle holder for covering the needle tip in the protective position.

20. The IV-catheter insertion device according to claim 16, wherein the depressible lever or press-button is pivotably connected to the protective barrel.

21. The IV-catheter insertion device according to claim 16, wherein the single depressible lever or press-button comprises a retaining hook extending radially inward.

* * * * *